(12) United States Patent
Steindahl et al.

(10) Patent No.: US 10,905,849 B2
(45) Date of Patent: *Feb. 2, 2021

(54) TEAR OPENABLE CATHETER ASSEMBLY

(71) Applicant: DENTSPLY IH AB, Mölndal (SE)

(72) Inventors: Thomas Steindahl, Myggenäs (SE); Kristina Eklöf, Mölndal (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/748,592

(22) Filed: Jan. 21, 2020

(65) Prior Publication Data

US 2020/0155795 A1 May 21, 2020

Related U.S. Application Data

(63) Continuation of application No. 15/790,411, filed on Oct. 23, 2017, now Pat. No. 10,569,046.

(30) Foreign Application Priority Data

Oct. 24, 2016 (EP) .................................. 16195265

(51) Int. Cl.
*A61M 25/00* (2006.01)
*B65D 75/58* (2006.01)
(Continued)

(52) U.S. Cl.
CPC ...... *A61M 25/002* (2013.01); *A61M 25/0017* (2013.01); *B65D 75/5816* (2013.01);
(Continued)

(58) Field of Classification Search
CPC ............ A61M 25/002; A61M 25/0017; A61M 2210/1085; A61M 2025/0046;
(Continued)

(56) References Cited

U.S. PATENT DOCUMENTS 2,923,404 A 2/1960 Adell
5,228,782 A 7/1993 Imer
(Continued)

FOREIGN PATENT DOCUMENTS

EP 1982741 A2 10/2008

OTHER PUBLICATIONS

European Search Report for European Patent Application No. 16195265.0, dated Apr. 6, 2017 (14 pages).

*Primary Examiner* — J. Gregory Pickett
*Assistant Examiner* — Tia Cox
(74) *Attorney, Agent, or Firm* — Perkins Coie LLP

(57) ABSTRACT

A medical device assembly is disclosed, comprising a medical device, such as a urinary catheter, and preferably having a hydrophilic surface coating, and a package forming a closed compartment around the catheter. The package is formed of at least one sheet of tearable material and comprises a first weld extending along a first side in a first direction of the package and a second weld extending along a second side in a second direction of the package. The first and second directions are different and preferably orthogonal to each other. A tear line is provided in the second weld, and arranged to direct a subsequent tear towards the first weld. Further, the first weld is provided with an inward protrusion, protruding inwardly towards the closed compartment, at a distance from the second weld. A corresponding method of production is also disclosed.

20 Claims, 3 Drawing Sheets

(51) Int. Cl.
*A61B 50/30* (2016.01)
*A61M 27/00* (2006.01)
*A61F 5/44* (2006.01)
*A61L 29/08* (2006.01)

(52) U.S. Cl.
CPC .......... *A61B 2050/314* (2016.02); *A61F 5/44* (2013.01); *A61L 29/08* (2013.01); *A61M 27/00* (2013.01); *A61M 2025/0046* (2013.01); *B65D 2575/3227* (2013.01); *B65D 2575/362* (2013.01); *B65D 2575/367* (2013.01)

(58) Field of Classification Search
CPC ........ B65D 83/10; B65D 75/30; B65D 75/58; B65D 75/5805; B65D 75/5816
USPC ...... 206/363, 571, 210, 438, 570–1; 53/412, 53/443; 383/200, 207, 209
See application file for complete search history.

(56) References Cited

U.S. PATENT DOCUMENTS

| | | | |
|---|---|---|---|
| 5,593,229 A * | 1/1997 | Warr | B65D 33/08 383/209 |
| 6,352,365 B1 | 3/2002 | Healy et al. | |
| 6,402,379 B1 * | 6/2002 | Albright | B65D 75/5816 383/209 |
| 6,848,574 B1 * | 2/2005 | Israelsson | A61M 25/002 206/210 |
| 9,033,149 B2 * | 5/2015 | Terry | B65D 65/38 206/364 |
| 10,071,833 B2 * | 9/2018 | Haedt | B65D 75/5827 |
| 2001/0001443 A1 | 5/2001 | Kayerod et al. | |
| 2003/0016889 A1 * | 1/2003 | Ichikawa | B65D 33/2508 383/204 |
| 2003/0118254 A1 | 6/2003 | Razeti et al. | |
| 2005/0109648 A1 * | 5/2005 | Kerzman | A61M 25/0111 206/364 |
| 2005/0199521 A1 * | 9/2005 | Givens, Jr. | A61M 25/002 206/364 |
| 2006/0163097 A1 * | 7/2006 | Murray | A61M 25/002 206/364 |
| 2007/0289887 A1 * | 12/2007 | Murray | A61M 25/0111 206/364 |
| 2008/0063324 A1 | 3/2008 | Bernard et al. | |
| 2008/0233252 A1 | 9/2008 | Manning et al. | |
| 2009/0116768 A1 | 5/2009 | Huerta et al. | |
| 2009/0131917 A1 * | 5/2009 | Kavanagh | A61M 25/0111 604/544 |
| 2011/0114520 A1 * | 5/2011 | Matthison-Hansen | A61M 25/002 206/364 |
| 2014/0174042 A1 | 6/2014 | Ezaki et al. | |
| 2016/0038713 A1 * | 2/2016 | Kearns | A61M 25/0111 206/210 |

* cited by examiner

TEAR OPENABLE CATHETER ASSEMBLY

CROSS-REFERENCE TO RELATED APPLICATIONS

This patent application is a continuation of U.S. patent application Ser. No. 15/790,411, filed Oct. 23, 2017, which further claims the benefit of and priority to European Patent Convention Application No. 16195265.0, filed on Oct. 24, 2016, which are herein incorporated by reference in their entirety.

FIELD OF INVENTION

The field of invention of the disclosed technology generally relates to medical devices and tear openable packages accommodating the medical devices.

BACKGROUND

The disclosed technology relates to a medical device assembly, and in particular for urinary hydrophilic catheters. Catheters are commonly used for draining bodily fluids, e.g. from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

However, there is still a need for improved packages for such catheter assemblies. The package should preferably be relatively simple and cost-efficient to produce. Further, the package should be easy to open, even for users with reduced dexterity. Still further, the package should enable adequate wetting of the catheter, and handling of the package in a clean manner. The package should also preferably be rather small, so that it can easily be carried around by the user in his/her daily life.

Many known catheter assemblies have tear openings. However, generally for known catheter assemblies with tear openings, the packages are difficult and cumbersome to open for the users, and in particular for users having reduced dexterity. In particular, both initiation and stop of the tearing action are difficult to control. The users often have problems in initiating the tear in the intended way. For example, one large group of users are people with injury in the spine, and a common side effect of this is that they have less natural moisture on the hands from perspiration, and hence their hands are dryer, with less friction in the grip. Specifically, the combination of less friction in the grip and limited dexterity affects the opening control, and when applying a pulling force, there is difficulty in starting the action in a controlled way. Also, stopping of the tearing action is problematic for the same reasons. It is generally very difficult to stop the tearing action in time once the tearing has started. Thus, there is a great risk of the so-called over opening. When over opening occurs, the medical device may inadvertently fall out, or in other ways be overly exposed in such a way that it may become contaminated prior to use. There is also a great risk of spillage of the wetting liquid and the like arranged together with the medical device in the package. Further, there is a great risk that the tear, once initiated, will progress in unwanted and unintended directions, which also will lead to either inadequate opening or over opening of the package.

In conclusion there is still a need for an improved medical device assembly of the above discussed general type.

SUMMARY

It is therefore an object of the disclosed embodiments to provide a medical device assembly which at least alleviates the above-discussed problems.

This object can be obtained by means of a medical device assembly and a method in accordance with the appended claims.

According to a first aspect of the disclosed embodiments there is provided a medical device assembly comprising a medical device, preferably having a hydrophilic surface coating, and a package forming a closed compartment accommodating said medical device, wherein the package is formed of at least one sheet of tearable material and comprising a first weld extending along a first side in a first direction of the package and a second weld extending along a second side in a second direction of the package, the first and second directions being different and preferably orthogonal to each other, wherein a tear line is provided in said second weld, the tear line being arranged to direct a subsequent tear towards the first weld, and wherein the first weld is provided with an inward protrusion, protruding inwardly towards said closed compartment, at a distance from said second weld.

This package is relatively simple and cost-effective to produce. At the same time, the package is very easy to open and use even for users having poor or reduced dexterity. The package may easily be opened by simply pulling the package on either side of the tear line apart, thereby tearing the package open. Further, the directivity provided by the tear line ensures that the subsequent tear occurs in a controlled way, towards the long side having the first weld. Still further, the inward protrusion of this first weld forms an efficient stop for the tear, thereby preventing further tearing when the tear reaches the inward protrusion.

The medical device assembly hereby ensures that opening occurs in the same way every time, in a very controlled way, and that the tear stops at a predetermined, controllable position. Hereby, it is ensured that the package is adequately opened, enabling easy withdrawal of the medical device, and at the same time, it is ensured that the package does not inadvertently open too much. Hereby, so called over opening is efficiently avoided, and it is ensured that the medical device does not inadvertently fall out of the package during opening, or being overly exposed, thereby preventing contamination of the medical device prior to use. It is further ensured that any wetting liquid or the like stored within the package is not spilled, or at least that the risk of spillage is significantly lowered.

Still further, this opening action is easily understandable in an intuitive way, facilitating opening of the package also for inexperienced users.

By "tear line" is, in the context of the present application, meant a line of weakness, perforations or even complete cut through. The tear line may be formed as a line of diminished material thickness, possibly extending over the entire thickness, providing a complete cut-through, arranged intermittently or continuously over the tear line. Continuous or discrete weakening may also be provided in other ways. Hence, the tear line may be a line with continuous or discontinuous perforations or other forms of weakening. Thus, in the context of the present application, "tear line" is used to indicate a line forming a weakening, such as a total cut-through, a partial cut-through, point perforations, or any other type of weakening, forming a weakening along a line where a rupture will occur when a force is exerted on the material.

The tear line may be arranged as a curved line or angled line, but is preferably arranged as an essentially straight line. This enables an easy and controllable pull through of the tear.

The tear line, or at least the part of the tear line being closest to the inward protrusion, is preferably slanted in relation to the first direction, and consequently forms an angle relative to the length direction of the package. Preferably, this angle is in the range of 10-60 degrees, and preferably 15-45 degrees, and most preferably 20-35 degrees.

The package is preferably elongate, and preferably having a rectangular shape, so that the first direction corresponds to a length direction of the package, and the second direction corresponds to a transversal direction of the package. In this case, the first side would constitute one of the two a long sides of the package, and the second side would constitute one of the two short sides. However, the package may alternatively have a square shape, thereby having the same extension in both the first and the second directions. Further, the first and second directions need not necessarily be perpendicular to each other, but may in some embodiments also assume other angles.

Further, the tear line is preferably arranged at a distance from both ends of the second weld, i.e. at a distance from both long sides of the package in case of an elongate package. Hereby, gripping tabs are formed on each side of the tear line, which are easily graspable by the user. Most preferably, the tear line is arranged essentially in the middle of the package, providing gripping tabs of essentially the same size on each side.

The first weld is preferably formed with two or more weld portions having different widths, a first weld portion being arranged between the second weld and the inward protrusion having a lower width than a second weld portion forming said inward protrusion. The second weld portion then preferably extends with the same width all the way to the opposite end of the package. However, other weld portions, having greater or lower widths, may also be provided. Further, each weld portion preferably has a generally uniform width. However, one or more weld portion may also have a varying width over its extension, thereby forming e.g. a tapering weld in any direction. The different weld portions may be produced one at a time, or simultaneously, e.g. using a welding abutment surface corresponding to the desired shape of the weld.

The inward protrusion preferably forms a stop line extending essentially perpendicular to the first direction of the package. However, the stop line may alternatively be beveled, e.g. forming an angle in the range of 60-120 degrees in relation to the first direction, and preferably in the range 70-110, and more preferably in the range 80-100.

In case a beveled stop line is wanted, a transition weld portion may be provided between the first weld portion and the second weld portion, providing a gradual transition between the width of the first weld portion and the width of the second weld portion.

Further, a second tear line may be provided in the first weld, said second tear line extending between a first position at the periphery of the first weld, and into the first weld in a direction towards the second weld. This second tear line thereby provides a second opening alternative, enabling the package to be opened in at least two different ways. This second opening alternative is also very intuitive, and provides a highly controllable opening action. Since the opening here occurs in the direction towards the second weld, the tear ends either when it reaches the second weld, or alternatively continuous through the second weld. However, since the starting point is predefined, over-opening of the package is efficiently avoided.

The provision of two entirely different opening actions is highly advantageous, since it facilitates opening for many users having varying reductions in dexterity. For example, the tear opening with the first opening action, with the first discussed tear line, can be made by simply applying pressure on the gripping tabs and pulling them apart, which can be performed by a simple clamping action by both hands. The second opening action can e.g. be performed with only one hand, holding the lower end of the package with the legs, arm or the like. The pulling action may here also be performed by twisting a gripping tab around the finger or the like to provide more friction. This upward pulling action may also be performed with the teeth or the like.

The second tear line preferably forms a first portion extending from said first position and into the first weld, a second portion extending generally in the first direction of the package, and an third portion extending in an inward direction. The first and third portions may preferably be at least to some extent curved. The first and third portion may hereby form a relatively long gripping tab, and the tear line is here preferably entirely cut-through.

Thus, at least a part of the second tear line, starting from the first position, is a cut through line forming a gripping tab.

The second tear line preferably extends from the first position to a second position, said second position being farther from the second weld than said inward protrusion. Hereby, the start of the tearing performed by the second tear line occurs on the opposite side of the inward protrusion in relation to the stop of the tearing performed by the firstly discussed tear line. The protrusion is preferably arranged to form a stop that prevents a tear along the first tear line to protrude into the second tear line.

The medical device is preferably a catheter, and preferably a urinary catheter, and most preferably a urinary catheter for intermittent use. In particular, the medical device is preferably a hydrophilic urinary catheter for intermittent use. However, even though the catheter assembly is at present primarily intended for urinary hydrophilic catheters, and most preferably where the package also includes a wetting fluid, the catheter assembly may also be used for other types of catheters. For example, the catheter may be other types of catheters, such as vein catheters and the like. Further, the catheter may be provided with other types of lubricious coatings, such as gel lubricants and the like, or being without any surface coating at all. Still further, assemblies without a wetting fluid are also feasible. Still further, the disclosed assembly may also be used for other types of medical devices than catheters.

The assembly further preferably comprises a wetting fluid for activation of the hydrophilic surface coating, wherein the wetting fluid is accommodated by the package. In a preferred line of embodiments, the wetting fluid is arranged in direct contact with the medical device, thereby maintaining the hydrophilic surface coating wetted during storage.

Hereby, when the medical device is a urinary catheter, there is provided a urinary catheter which is immediately ready-for-use. However, alternatively, the wetting liquid may be arranged in a separate compartment during storage, such as in an integral separate compartment of the same package, or in a separate container, such as a sachet, ampoule or the like. In such embodiment, the separate compartment is opened prior to use, preferably without breaking the integrity of the package, for release of the wetting liquid into the compartment housing the medical device, for wetting of the hydrophilic surface coating. Release of the wetting fluid can be obtained by squeezing, bending or the like, as is per se well known in the art.

The package is formed by sheet material, and preferably by foil sheet material. The sheet(s) may be formed entirely by a weldable material. However, preferably, the sheet(s) comprise laminated sheet(s), having a weldable inner layer and a protective outer layer. The sheet material is also preferably a flexible material.

The at least one sheet preferably provides first and second side panels of the package. In one embodiment, two sheets may be provided, each forming one of said side panels, and being connected around the edges. However, alternatively a single sheet may be provided and forming said two side panels. Hereby, at least one side connection is formed by a fold of the sheet material.

According to another aspect of the disclosed embodiments, there is provided a method of producing a medical device assembly comprising the steps:

providing a medical device, preferably having a hydrophilic surface coating or being formed of a hydrophilic material; and accommodating the medical device in a closed compartment of a package formed of a tearable material, said package comprising:

a first weld extending along a first side in a first direction of the package and a second weld extending along a second side in a second direction of the package, said first and second directions being different and preferably orthogonal to each other, wherein a tear line is provided in said second weld, the tear line being arranged to direct a subsequent tear towards the first weld, and wherein the first weld is provided with an inward protrusion, protruding inwardly towards said closed compartment, at a distance from said second weld.

These and other aspects of the disclosed embodiments will be apparent from and elucidated with reference to the embodiments described hereinafter.

BRIEF DESCRIPTION OF THE DRAWINGS

For exemplifying purposes, the disclosed technology will be described in closer detail in the following with reference to embodiments thereof illustrated in the attached drawings, wherein.

DETAILED DESCRIPTION OF PREFERRED EMBODIMENTS

Figure 1:
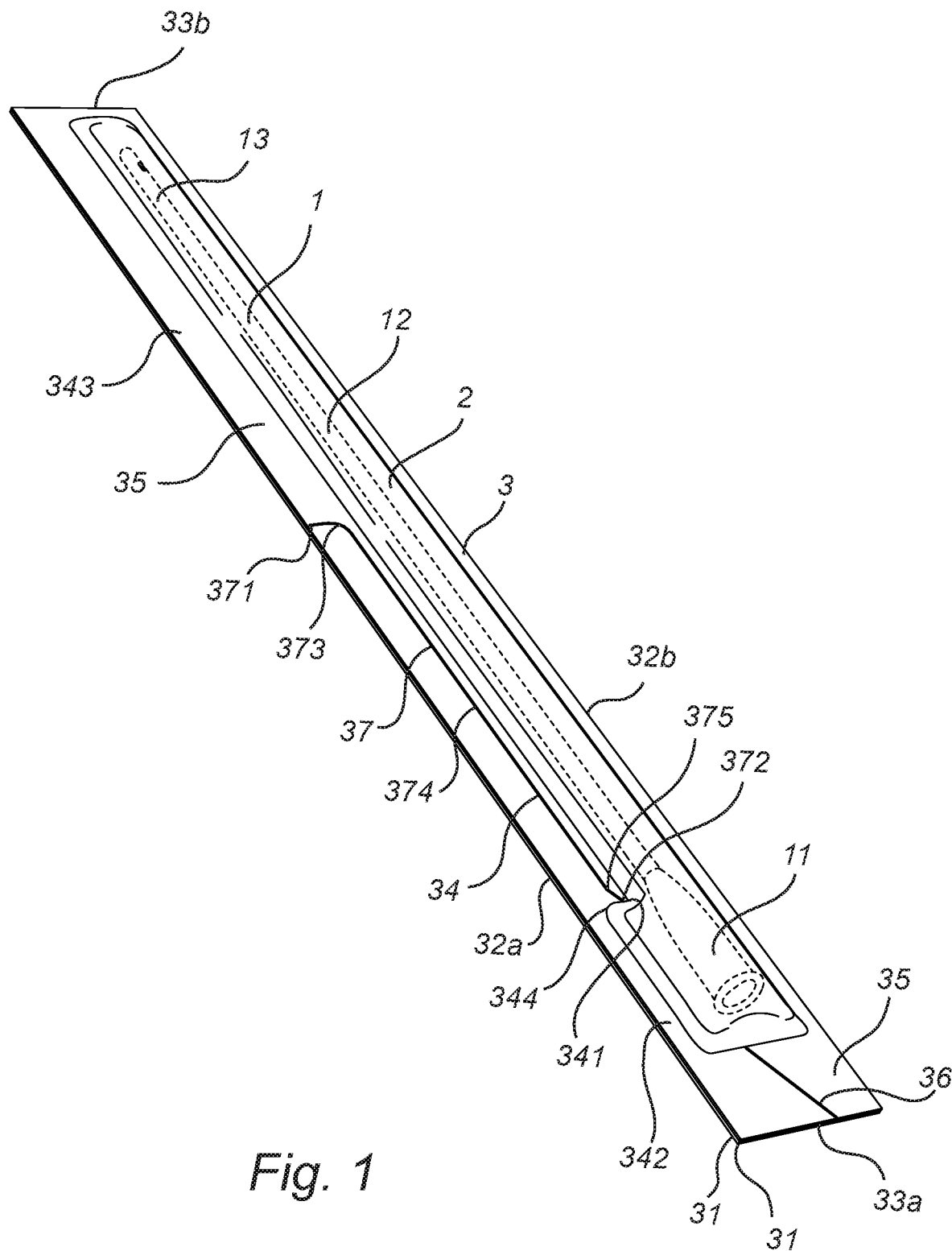
FIG. 1 is a perspective view of a medical device assembly in a closed position in accordance with an embodiment of the disclosed technology.
Figure 2:
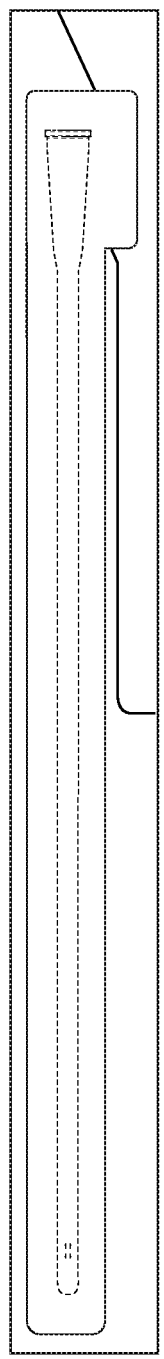
FIG. 2 is a top view of the medical device assembly of FIG. 1 in the same closed position.

In the following detailed description preferred embodiments of the disclosed technology will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the disclosed embodiments, e.g. the length of the medical device, etc.

The medical device assembly can be used for many types of medical devices. However, it is particularly suited for catheters. Catheters may be used for many different purposes, and for insertion into various types of body-cavities. However, the following discussion is in particular concerned with the preferred field of use, hydrophilic urinary catheters, even though the disclosed technology is not limited to this particular type of catheters, and also not to catheters.

The package disclosed in relation to the illustrative example has a rectangular, elongate shape. However, as discussed in the foregoing the package may also have other shapes, such as being of a square shape. Thus, any reference to length direction, longitudinal or long side, short side, transverse direction, etc. will, when applied to packages of other shapes, not necessarily mean that the long side is longer than the short side, that the length direction is the longest direction, that the transversal direction is perpendicular to the length direction, etc.

The catheter assembly as illustrated in FIGS. 1-4 comprises a catheter 1 having a hydrophilic surface coating, optionally a wetting fluid 2 for activation of said hydrophilic surface coating and a package 3 accommodating the catheter and the wetting fluid.

The catheter 1 may be any type of hydrophilic catheter, as is per se well known in the art. Preferably, the catheter comprises an enlarged rearward portion, e.g. forming a flared or frusto-conical connector 11, and an elongate shaft 12, connected to the connector 11, and in the opposite end having a catheter insertion end 13. Further, the catheter may also end directly at the end of the elongate shaft, without any connector, or be provided with other type of rearward arrangements.

At least a part of the elongate shaft 12 forms an insertable length to be inserted through a body opening of the user, such as the urethra in case of a urinary catheter. At least the insertable length is preferably, in the context of a hydrophilic catheter, provided with a hydrophilic surface, such as a hydrophilic surface coating, for example Polyvinylpyrrolidone (PVP), and which provides a low-friction surface when wetted with a wetting fluid. Typically, the insertable length is within 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride.

The wetting fluid for activation of the catheter need not be provided within the package. Instead, a wetting fluid may be poured into the package after opening of the package, for wetting of the catheter while it still remains in the package. In some occasions, the catheter may even be removed from the package and wetted e.g. in a different container, even though this is normally not preferred.

However, preferably the wetting fluid is arranged within the package, so that the hydrophilic surface of the catheter can be activated even before opening of the package. In one embodiment, the wetting fluid is arranged separated from the catheter, in a wetting fluid container (not shown), such as a pouch or a sachet. The wetting fluid container is openable by means of e.g. exerting a pressure to the container, whereby the wetting fluid is released into the package, thereby wetting the hydrophilic surface of the catheter. In another embodiment, the wetting fluid is arranged directly in the compartment of the package which also houses the catheter, so that the hydrophilic surface of the catheter is in direct contact with the wetting fluid during storage, and thereby is maintained in an activated, ready-to-use state.

The wetting fluid is preferably a liquid, and most preferably an aqueous liquid, such as water or saline. However, the wetting fluid may also be a gas, providing a moist atmosphere in the package sufficient for activation of the hydrophilic surface. Thus, the wetting fluid may be any fluid, gas or liquid, that wets/activates a hydrophilic surface of the catheter.

In the illustrative example, the package does not contain any wetting fluid.

The package is preferably made of sheet material. In the shown embodiment, the package is made of two sheet materials 31, connected around the edges to form an inner cavity housing the catheter and the optional wetting fluid. The first and second sheet materials are preferably connected around the edges by means of welding, forming welded edge joints. However, alternatively, a folded sheet material may also be used for forming the package, whereby one or several sides of the package may be closed by the fold instead of, or in addition to, the weld. The sheet material may also be provided in the form of a tube, requiring even less welded joints to close the package. However, depending on which sides that are closed, additional welds along the closed sides may still be required to form the tear lines, protrusions, etc., as discussed in the following.

The sheet material is preferably a tearable material, and preferably comprises a laminated sheet material, and preferably having a weldable inner layer and a protective outer layer.

The sheet materials are preferably of a flexible plastics material. The material may be transparent, but opaque or semi-opaque materials may also be used. For example, the sheets can be made of polymer materials such as polyethene (PE), polypropylene (PP), polyamide (PA), poly(ethylene terephthalate) (PET), oriented polypropylene (OPP), oriented polyamide (OPA), etc. Also, the receptacle can be made of one or several materials functioning as barrier material or having low water vapor transmission. The material of the sheet material, or the material of one of the layers in case of a laminate, may to this end comprise or consist of one or several of aluminum, aluminum oxide, silicone oxide, metallocene polyvinylidene chloride (PVdC) and poly(ethylene-vinylalcohol) (EVOH). For example, the flexible material can be made as coextruded polyolefines with polyamides, poly(ethylene terephthalate) (PET), including barrier resins such as polyvinylidene chloride (PVdC) or poly(ethylene-vinylalcohol) (EVOH). However, other materials exhibiting similar properties are also feasible.

The package 3 is formed as an elongate package, comprising two first, longitudinal sides 32a and 32b, extending in a first, length direction of the package, and two second, short sides, 33a and 33b, extending in a second, transversal direction of the package. All sides are closed, thereby forming a closed compartment accommodating the medical device in a sterile way. Preferably, the package is arranged to maintain sterility during a prolonged storage. The assembly preferably has a shelf life of at least 2 years, and most preferably at least 3 years.

The longitudinal sides and short sides may be closed in various ways, such as by welded joints, by folding, etc. However, a first weld 34 is arranged along the first longitudinal side 32a, this first weld thereby extending along in a first, length direction of the package, and a second weld 35 is arranged along the first short side 33a, this second weld thereby extending in a second, preferably transversal direction of the package.

The first weld 34 comprises an inward protrusion 341, protruding inwardly towards the closed compartment at a distance from the second weld 35. Specifically, the first weld may be formed with two or more weld portions having different widths. In the disclosed embodiment, the first weld comprises a first weld portion 342 being arranged between the second weld and the inward protrusion having a relatively low width, and a second weld portion 343 forming the inward protrusion 341, and preferably extending over the rest of the longitudinal side. The second weld portion 343 here has a relatively greater width, so that the first weld portion 342 has a lower width than the second weld portion 343, thereby forming a knee in the transition, forming said protrusion 341. Each weld portions may have a generally uniform width, or alternatively, the width of the weld portions may vary to a small or great extent.

However, the longitudinal first weld may also be provided in other ways. For example, the protrusion may be formed by an intermediate weld portion having greater width, with weld portions of lower width on both sides. One or several of the weld portions may also have a width variation, for example providing a gradual or stepwise transition between sections of greater width and sections with lower width. In particular, there may be provided a transition weld portion 344 between the above-discussed first weld portion and second weld portion, providing a gradual transition between the width of the first weld portion and the width of the second weld portion.

At least one tear line is further provided for tear opening of the package. In the disclosed exemplary embodiment, two different tear openings are provided.

A first tear line 36 is arranged in the first short side 33a, at least partly extending through the second weld 35. The tear line may be arranged as a curved line or angled line, but is preferably arranged as an essentially straight line. The tear line 36 is further arranged in a slanted disposition relative to the length direction of the package, so that the tear line is directed towards the first weld. Alternatively, only a part of the tear line may be arranged in this slanted disposition. The tear line, or part of the tear line, may e.g. form an angle relative to the length direction of the package in the range of 10-60 degrees, and preferably 15-45 degrees, and most preferably 20-35 degrees. However, other ways of providing a directivity of the tear line directing the subsequent tear in the desired direction may also be contemplated. The tear line 36 is further preferably arranged substantially centrally on the short side 33a, at a distance from both long sides 32a and 32b of the package.

Figure 3:
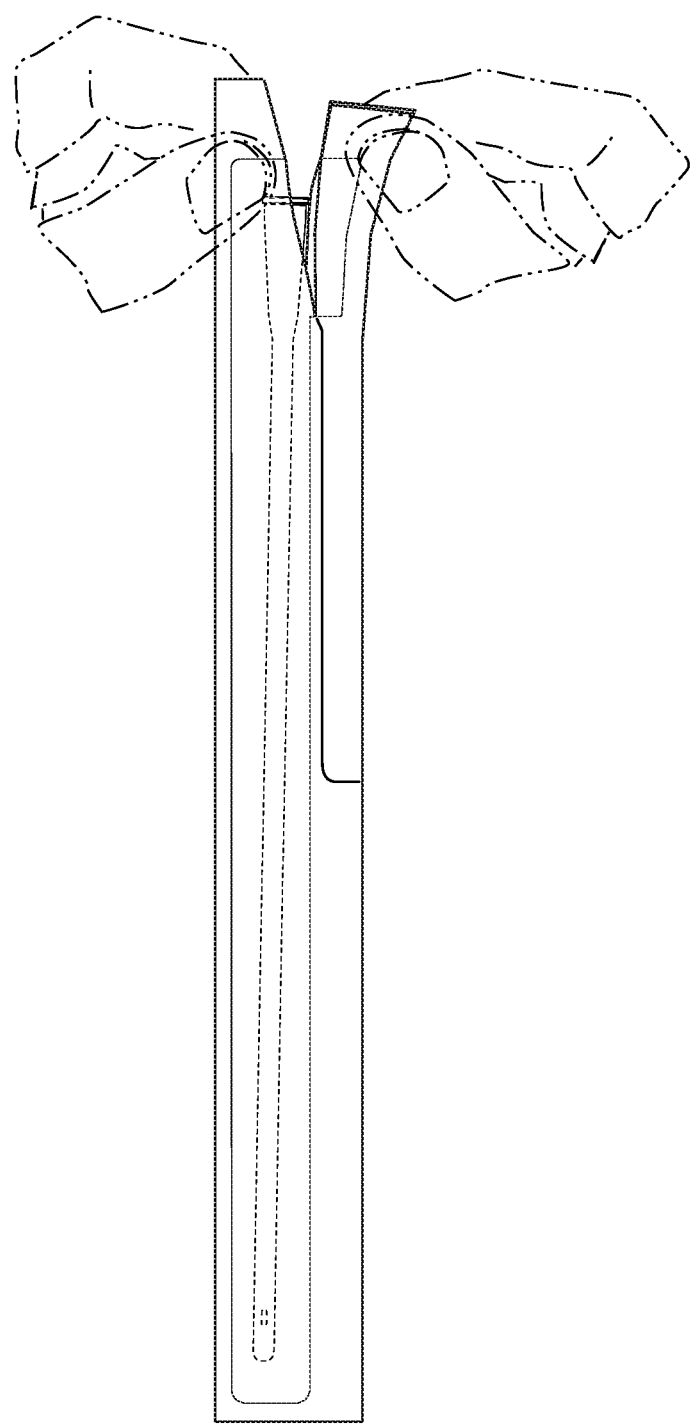
FIG. 3 is a top view of the medical device assembly of FIG. 1 in a first opened position.

When opening the package with the first tear line 36, as illustrated in FIG. 3, the user grips the areas of the package arranged on both sides of the tear line 36, and pulls the gripping areas apart. Hereby, the package is torn open. Further, the slanted disposition of the tear line ensures that the tear occurs in a controlled way, towards the long side 32a having the first weld 34. Still further, the inward protrusion

341 of this first weld forms an efficient stop for the tear, thereby preventing further tearing when the tear reaches the inward protrusion, as illustrated in FIG. 3.

A second tear line 37 is provided in the first weld 34. This second tear line 37 extends between a first end position 371 at the periphery of the first weld, and into the first weld in a direction towards the second weld, to a second end position 372. The second tear line 37 preferably forms a first portion 373 extending from the first end position 371 and into the first weld, a second portion 374 extending generally in the length direction of the package, and an third portion 375 extending in an inward direction. The second end position is preferably arranged farther from the second weld 35 than the inward protrusion 341.

At least a part of the second tear line 37, starting from the first position 371, is preferably a cut through line forming a gripping tab. Alternatively, the gripping tab may be connected to the rest of the package with a faint joint, such as using a weakening which is not a complete cut through, or by maintaining one or some few areas of interconnection in an otherwise complete cut through line.

Figure 4:
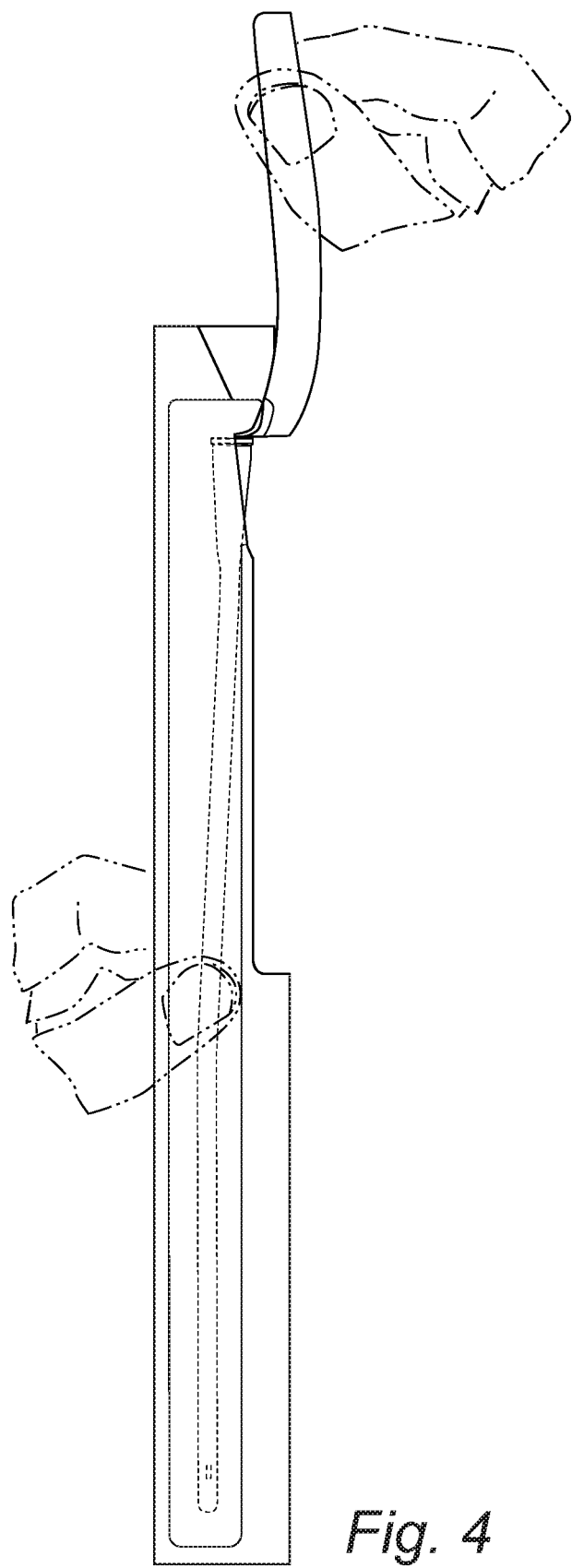
FIG. 4 is a top view of the medical device assembly of FIG. 1 in a second opened position.

Opening of the package with the second tear line 37 is illustrated in FIG. 4. By gripping the tear line at a gripping area close to the first end position 371, the gripping tab is pulled upwardly, towards the second weld 35. Hereby, the package is torn open. Further, due to the slanted disposition of the third portion 375, the tear is directed inwardly. The pulling may be arranged to be stopped by the second weld 35, as shown in FIG. 4. However, alternatively, the tear may be allowed to proceed towards the end of the package, thereby providing a complete opening of the package.

The catheter is preferably oriented in such a way in the package that the non-insertable part, here the connector end, is arranged closest to the second weld 35. Hereby, opening by any of the tear opening actions discussed above will open the package in such a way that the non-insertable part of the catheter, here the connector, is exposed, whereas the insertable part of the catheter is still residing unexposed in the package. This allows the catheter to be pulled out of the package by gripping this non-insertable part (connector), in a clean, aseptic way. Further, the part of the catheter having the largest diameter, i.e. the connector, will hereby reside in a part of the package having the greatest dimensions, i.e. in the part of the package extending between the inward protrusion 341 and the second weld 35. This makes it possible to provide a very slim package, narrowly surrounding the catheter.

A method of manufacturing the above-discussed catheter assembly preferably comprises the following steps of producing the package, performed in any order:

Providing one or several sheet material(s);

Providing a catheter;

Forming the sheet material(s) to a package to accommodate the catheter, by folding the sheet material or by arranging two or more sheets on top of each other;

Optionally arranging a wetting fluid within the package;

Connecting the edges of the package, and especially forming the above-discussed first and second welds and the tear line(s); and Sterilizing the package together with its content, e.g. by means of irradiation.

Specific embodiments of the disclosed technology have now been described. However, several alternatives are possible, as would be apparent for someone skilled in the art. For example, although the wetting fluid in the described embodiments is arranged in direct contact with the catheter, but may alternatively be arranged separated from the catheter, in a wetting fluid container. Further, it is possible to use only one of the two tear lines discussed above, or alternatively to provide further tear opening facilities. Further, the inward protrusion of the first weld may be arranged in various ways. Such and other obvious modifications must be considered to be within the scope of the present invention, as it is defined by the appended claims. It should be noted that the above-mentioned embodiments illustrate rather than limit the disclosed technology, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A medical device assembly comprising a medical device and a package forming a closed compartment accommodating said medical device, wherein the package is formed of at least one sheet of tearable material and comprising a first weld extending along a first side in a first direction of the package and a second weld extending along a second side in a second direction of the package, said first and second directions being different, wherein a tear line is provided in said first weld, the tear line being arranged to direct a subsequent tear towards the second weld, and wherein the first weld is provided with an inward protrusion, protruding inwardly towards said closed compartment, at a distance from said second weld, wherein the first weld is formed with two or more weld portions having different widths, a first weld portion of the first weld being arranged between the second weld and the inward protrusion and having a lower width than a second weld portion of the first weld forming said inward protrusion, wherein the tear line extends between a first position at the periphery of the first weld portion of the first weld, and into the first weld in a direction towards the second weld.

2. The medical device of claim 1, wherein the medical device is provided with a hydrophilic surface coating or is formed of a hydrophilic material.

3. The medical device of claim 1, wherein the first and second directions are orthogonal to each other.

4. The medical device of claim 1, wherein the first weld comprises a transition weld portion provided between said first weld portion and said second weld portion, providing a gradual transition between the width of the first weld portion and the width of the second weld portion.

5. The medical device of claim 1, wherein the tear line forms a first tear line portion extending from said first position and into the first weld, a second tear line portion extending generally in the first direction of the package, and a third tear line portion extending in an inward direction.

6. The medical device of claim 4, wherein the tear line extends from the first position to a second position, said second position being provided in the transition weld portion of the first weld.

7. The medical device of claim 1, wherein the tear line extends from the first position to a second position, said second position being farther from the second weld than said inward protrusion.

8. The medical device of claim 1, wherein at least a part of the tear line, starting from the first position, is a cut through line forming a gripping tab.

9. The medical device assembly of claim 1, wherein the medical device is a catheter.

10. The medical device assembly of claim 1, wherein the medical device is a urinary catheter.

11. The medical device assembly of claim 1, wherein the medical device is a urinary catheter for intermittent use.

12. The medical device assembly of claim 2, wherein the assembly further comprises a wetting fluid for activation of said hydrophilic surface coating or said hydrophilic material, said wetting fluid being accommodated by said package.

13. The medical device assembly of claim 12, wherein the wetting fluid is arranged in direct contact with the medical device, thereby maintaining the hydrophilic surface coating wetted during storage.

14. The medical device assembly of claim 1, wherein the sheet(s) comprises laminated sheet(s), having a weldable inner layer and a protective outer layer.

15. The medical device of claim 1, wherein a second tear line is provided in said second weld, said second tear line being arranged to direct a subsequent tear towards the first weld.

16. The medical device assembly of claim 15, wherein at least a part of the second tear line being closest to the inward protrusion is arranged in a slanted disposition relative to the first direction of the package.

17. The medical device assembly of claim 16, wherein the slanted disposition of the second tear line or a part of the second tear line forms an angle relative to the first direction of the package in the range of 10-60 degrees.

18. The medical device assembly of claim 16, wherein the slanted disposition of the second tear line or a part of the second tear line forms an angle relative to the first direction of the package in the range of 15 to 45 degrees.

19. The medical device assembly of claim 16, wherein the slanted disposition of the second tear line or a part of the second tear line forms an angle relative to the first direction of the package in the range of 20 to 35 degrees.

20. The medical device assembly of claim 15, wherein the second tear line is arranged at a distance from both ends of the second weld.

\* \* \* \* \*